United States Patent [19]

Olinger et al.

[11] 3,941,121

[45] Mar. 2, 1976

[54] FOCUSING FIBER-OPTIC NEEDLE ENDOSCOPE

[75] Inventors: Charles P. Olinger, Cincinnati, Ohio; Ronald L. Ohlhaber; Casey Kot, both of Chicago, Ill.

[73] Assignee: The University of Cincinnati, Cincinnati, Ohio

[22] Filed: Dec. 20, 1974

[21] Appl. No.: 534,779

[52] U.S. Cl. ............................. 128/6; 350/96 BC
[51] Int. Cl. ........ A61b 1/06; A61b 1/26; A61b 1/30
[58] Field of Search ............................. 128/4–8; 350/96 BC

[56] References Cited
UNITED STATES PATENTS

| | | | |
|---|---|---|---|
| 3,090,378 | 5/1963 | Sheldon et al. | 128/4 |
| 3,434,775 | 3/1969 | Gosselin | 128/6 |
| 3,556,085 | 1/1971 | Takahashi | 128/6 |
| 3,643,653 | 2/1972 | Takahashi | 128/6 |

OTHER PUBLICATIONS

A Wide-Angle Needle Endoscope, Published in Program of the Joint Meeting American Neurological Assoc. etc., 6-13-73.

*Primary Examiner*—Lawrence Charles
*Attorney, Agent, or Firm*—Wood, Herron & Evans

[57] ABSTRACT

A needle endoscope includes a hollow needle of about 18-gauge, a lens system within the needle, an image transmitting bundle of flexible fiber-optic rods within the needle, a plurality of illumination transmitting fiber-optic rods within the needle, an operative channel within the needle, and apparatus to shift the image transmitting bundle with respect to the lens system and needle to provide focus adjustment for focusing the endoscope on objects at various distances from the end of the needle. The channel is adapted to receive an electrode having an end which, when extended beyond the needle, can be microscopically viewed and supervised through the needle during application of radiofrequency pulses to the spinal cord's nerve tracts or nerve cells, for example. Both medical and industrial uses are contemplated.

40 Claims, 4 Drawing Figures

U.S. Patent March 2, 1976 3,941,121
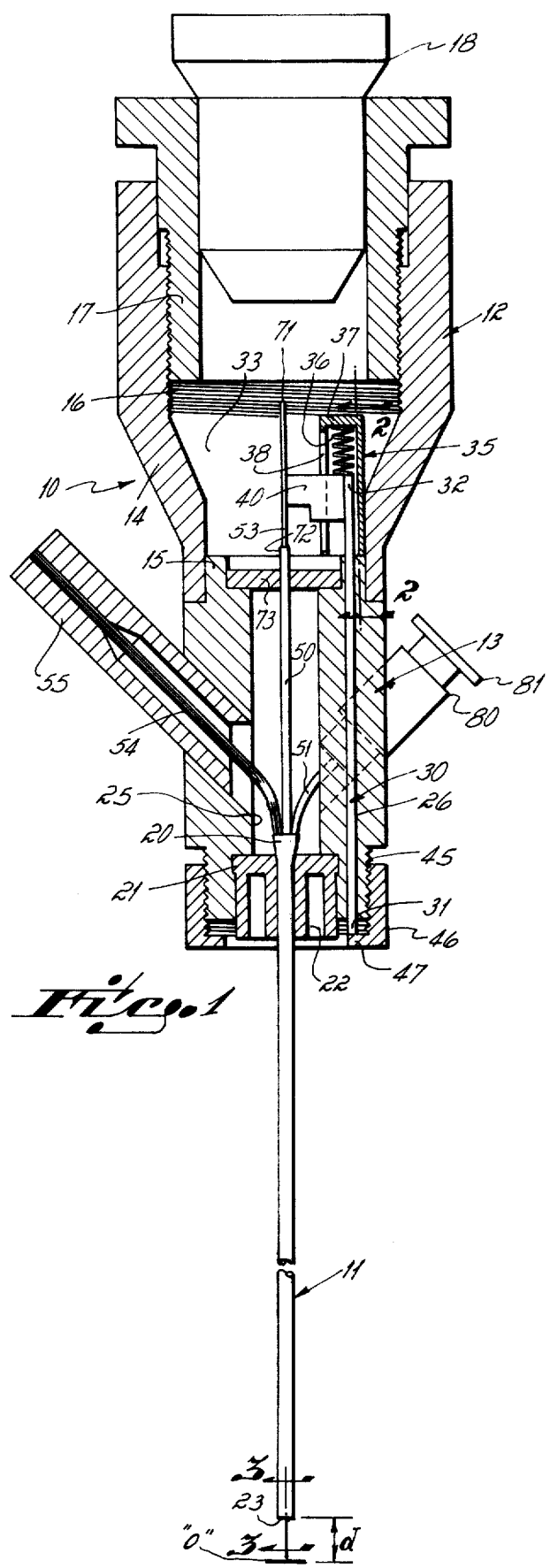
Fig.1
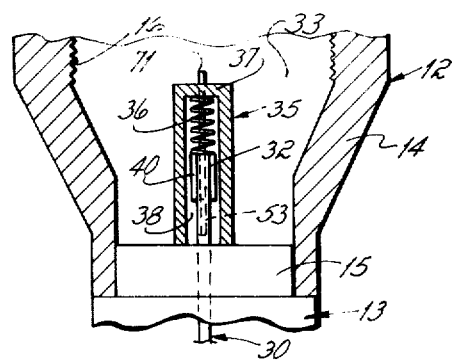
Fig.2
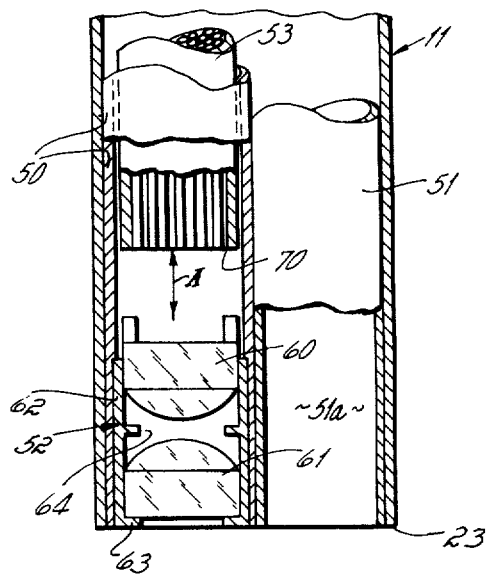
Fig.3
Fig.4

FOCUSING FIBER-OPTIC NEEDLE ENDOSCOPE

This invention described herein was made in the course of work under a grant or award from the Department of Health, Education and Welfare.

This invention relates to instruments for viewing and for treating objects in remote locations and particularly to a fiber-optic needle endoscope useful for observing, for studying and for treating internal body tissues and cells under both microscopic and telescopic conditions.

In treating patients having problems requiring inspection and treatment of the nervous system, such as for example, patients with intractable pain or spasticity, it is common to perform either open surgery cordotomy or to perform percutaneous methods for relieving the patient; such percutaneous methods including the destruction of certain spinal cord nerve cells or tracts by the insertion of instruments under essentially blind guidance techniques such as X-ray and the like. Such guidance techniques are not highly precise, and are difficult to perform with a high degree of efficiency when it is recognized that only a very few cells are to be treated.

In these percutaneous methods or in visualization techniques where the spinal cord is entered, or any other critically fragile and sensitive internal area of the body such as the eye, the brain or the heart is to be viewed or treated, smallness of the instrument used is of particular importance in order to avoid undesired damage or trauma, such as bleeding, to nerve cells or surrounding body tissues. When viewing the spinal cord, for example, bleeding could obscure the area to be viewed and must be avoided. Smallness is also critical to use of a viewing or treatment instrument in children where internal body areas and tissues are even smaller. From a practical safe usage standpoint, it has been found that while physicians may accept instruments of up to 14-gauge diameter, much smaller instruments of 18-gauge diameter, for example, are highly preferred, the larger instruments being considered less safe.

While it is thus desirable to maintain a minimum diameter in viewing or treatment instruments, this very smallness heretofore resulted in functional limitations. Some viewing instruments, for example, have been limited to viewing only objects contacted by the instrument or at set distances therefrom. Further, no treatment means is provided in any known viewing instrument of about 18-gauge or smaller.

As an example of prior instruments, viewing has been accomplished by optical viewing instruments such as that shown in U.S. Pat. No. 3,556,085. While some such instruments have been as small as 1.5 mm in diameter, they also have been relatively limited in functional capability due principally to their smallness. For example, the microscope described and shown in FIG. 1 of U.S. Pat. No. 3,556.085 is limited to the transmission of images of objects which the forward end of the microscope actually contacts. The microscope is apparently not functional to efficiently transmit images of objects spaced from the forward end of the microscope. Additionally, such microscope is limited to viewing only and provides no means for treating the tissues it inspects or for visually supervising such treatment.

For general viewing of spaced objects, the patent cited above provides an additional viewing instrument into which the microscope element is inserted. The additional instrument is substantially larger than the microscope, however, and may be too large for many applications. Further, the use of two optical viewing instruments is required.

In using an inspection instrument, it is desirable to view not only actually contacted objects but also to view, ahead of the instrument, the body tissues which are not contacted. With this capability, the user can properly orient the instrument and can view tissue or cells at a distance over a relatively wide field of view. In order to provide an endoscope which can be used both microscopically, in viewing objects under high magnification and resolution, and telescopically, in viewing objects further from the end of the instrument but at less magnification, it is necessary to provide an optical system which can be focused on images at varying distances from the end of the instrument.

In one attempt to provide adjustable focusing in a borescope instrument, U.S. Pat. No. 3,434,775 discloses a cable control extended within the borescope to a forward lens thereof. Rotation of the cable moves a forward lens with respect to the borescope and a fiber-optic bundle for focusing purposes. As is apparent from the patent, the diameter of the borescope must be sufficient to provide room, not only for illumination and image transmitting fibers, but for the control cable as well, no treatment means being provided. It thus appears from the art that if adjustable focusing is desired, the viewing instrument must be increased in size to accommodate the focusing control structure such as a control cable. Such size increases are undesirable, and endoscopes have heretofore been functionally limited as a result.

Thus, there is and has been for some time a need for a viewing and treatment instrument of very small diameter, on the order of 18-gauge, which can be used percutaneously with a precise degree of control without resort to essentially blind guidance techniques. While various attempts have been made at viewing internal body tissues, such as the spinal cord, none of these have produced an acceptably small instrument which provides an in-focus microscopic-telescopic inspection capability for a wide range of object-to-instrument distances, nor have any of these provided precise visual microscopic supervision of an operative member such as an electrode extended through the instrument.

Accordingly, it has been one objective of this invention to provide an acceptably smaller diameter needle endoscope which provides in-focus microscopic-telescopic viewing of objects spaced within a wide range of distances from the endoscope.

A further object of the invention has been to provide a versatile diagnostic or treatment needle endoscope which can be used to view and treat internal body tissues, is not limited to viewed object contact or to a single object-to-lens distance for image transmission, is capable of providing operative visual supervision of a treatment procedure performed through an operative channel of the needle and which is small enough to be universally acceptable for introduction into previously inviolate tissue area without resort to open surgery techniques or to essentially blind guidance techniques such as X-ray.

A further object of the invention has been to provide an acceptably small needle endoscope having means to focus the endoscope for in-focus viewing of objects at varying distances from the endoscope and including a treatment channel for instruments such as an electrode.

for example, which can be visually and microscopically supervised during use.

To these ends, the invention contemplates in a preferred embodiment, a fiber-optic needle endoscope of acceptably small diameter, having imaging, illumination and operative channels, the capability of visual microscopic supervision of an instrument extended from the operative channel, and focusing means for focusing the endoscope with respect to objects at varying distances from the needle, the needle being small enough to fit within a 17-gauge thin-wall lumbar puncture needle. The needle comprises an 18-gauge hollow needle having an image transmitting bundle of fibers, a plurality of illumination transmitting fiber-optic rods, an operative channel or tube, a lens system at the forward end of the needle and in register with the forward end of the image transmitting bundle, and means for reciprocating or shifting the bundle with respect to the lens system to focus an image transmitted by the lens system to the forward end of the bundle.

The focusing means includes a ring mounted on a scope body to which the needle is connected, and a rod having one end engaging the ring and another end connected to a rearward end of the image transmitting bundle. When the ring is turned on the scope body, the rod is moved and the bundle is likewise moved to shift its forward end with respect to the lens system and thereby focus the lens transmitted image. Since the bundle is reciprocated, no additional focusing structure is necessary within the needle itself and its outer diameter can be held to that desired.

The invention is particularly useful for inspecting, studying and treating the nervous system and particularly the spinal cord, as, for example, in making radiofrequency lesions in nerve tracts, under direct visual supervision, in patients with intractable pain or spasticity. Now, for the first time, an electrode may be inserted percutaneously into the spinal pathways under direct visual control to make radiofrequency lesions in patients with intractable pain. Using known anterior, lateral and posterior cordotomy, tractotomy and commissurotomy techniques, this method is then comparable to an open surgical trast, other current percutaneous methods resort to guidance by X-ray studies and other complicated and essentially blind techniques of limited use, none of which compensate for anatomical variation, spinal cord displacement or the presence of pial vessels as does the endoscope of the invention which is inserted under direct visual control.

In use, a 17-gauge, thin-wall lumbar puncture needle and stylet are inserted into the area of the spinal column. The stylet is withdrawn and the needle of the preferred embodiment is inserted. The endoscope is initially adjusted to focus "telescopically" on objects spaced from the end of the needle. A relatively wide field is viewed (area-location viewing) and the user can properly orient the needle. As the needle end approaches the nerve cells or tract focus is adjusted to keep the viewed cells in focus at the increasing level of magnification. The needle can thus be precisely placed during constant actual visual control.

Once the needle is in proper position, an electrode is inserted through the operative channel to extend beyond the needle's end. The end of the electrode can then be viewed through the instrument and it too can be precisely placed under direct microscopic supervision. Radiofrequency pulses are then applied to the electrode to produce a radiofrequency lesion interrupting the nerve tract. Alternately, the operative channel can be used for the injection or aspiration of fluids, biopsy sampling, etc.

For diagnostic or other visualization, the scope body is provided with an objective for magnifying the image transmitted from the lens system and forward end of the image bundle to the rear end of the image bundle. This objective can also be adjusted to maintain the image in focus. Additionally, adapters can be utilized to attach the scope body to a microscope, a camera, or to other diagnostic or viewing equipment.

The needle endoscope with its electrode channel provides a unique opportunity: (1) to study the spinal pain pathways in the cord; (2) to study the existence of "accessory pathways" for the central projection of pain impulses; (3) to study the mechanism of conduction and experience of pain in man; (4) to study the electrostimulation methods to inhibit central pain; (5) to explain loss of pain and retention of sharp or blunt sensation after commissurotomy; and (6) to explore the various theories of pain.

In addition to its structural features, the invention provides a method to relieve chronic intractable pain and which is non-addicting, non-surgical (not open), should not affect the personality of mind, and is only minimally destructive of neural tissue if at all.

In addition, the invention has a large and diverse applicability to a number of medical diagnostic and treatment fields since it opens the body to internal visual inspection without open surgery.

For example, by using the needle endoscope, diagnostic myeloscopy can now be extended safely beyond the lumbosacral area. Using known anterior percutaneous cordotomy methods, the needle endoscope can reach and visualize the anterior cervical canal and its contents. By inserting the endoscope through a guide needle passed through the alanto-occipital membrane into the cisterna magna or between C1 and C2 spinous processes and by using posterior percutaneous trigeminal tractotomy, myelotomy, and corodotomy methods, the floor of the fourth ventricle, the obex and the dorsal medullary area can be visualized. The posterior cervical and thoracic spinal cord might even be visualized with the endoscope by applying methods for diagnostic and therapeutic percutaneous needle punctures of syringomylelia cavities and intramedullary tumor cyst. The needle endoscope could also be used to visualize the high lateral and anterior cervico-medullary area by applying the lateral percutaneous cordotomy methods for intractable pain and now used for lateral cervical myelography.

Further, the needle endoscope with electrode channel should assist in understanding and treating the neurogenic bladder which remains a challenging problem in the care of paraplegic patients. It is contemplated that the endoscope might eventually permit needle electrode implantation or selective sacral rhizotomy without a laminectomy.

Many neurological disorders lead to exaggerated muscle tone which may result in violent, painful flexor spasms, deforming contractures, excoriation and ulceration. In certain paraplegic, quadraplegic or paraparetic patients, spasticity and spasm negate all efforts at rehibilitation. Treatment of severe spasticity of the legs is a difficult problem, as attested by the many surgical procedures and medical treatments tried over the years. For example, spasticity in man has been successfully treated through a longitudinal transverse myelotomy in patients with complete or partial paraplegia. The spasticity of decerebrate cats has been reduced by producing a radiofrequency lesion in the segmental motor neuron pool of the lumbosacral spinal cord. Persons performing such experimentation felt that a radiofrequency lesion which would selectively reduce the sensory inflow to the segmental and neighboring motor neuron pool might be even more effective in suppressing exaggerated reflex activity.

The minaturized needle endoscope with electrode channel provides the necessary access for reducing spasticity by interrupting pathways and centers in the cord without surgery; and obtains motor and bladder improvement with more regularity.

Still further, the endoscope of the invention provides a tool for use in diagnosing and treating spinal injuries. The need for new tools and methods in diagnosis, study and treatment of spinal cord injuries becomes urgent as evidence increases that the first few hours after injury are critical if progression of spinal cord degeneration is to be prevented. Already the course of paraplegia in animals and in a limited number of human beings has been modified to some extent by the use of hypothermia, corticosteroids, hyperbaric oxygen and the blocking of norepinephrine synthesis by alphamethyl tyrosine which help preserve the circulation and oxygenation of neurons in the first few hours after spinal cord injury. With the in vivo microscope-telescope provided by the invention and with the electrode channel, the needle endoscope lends itself to the early study of the neurophysiological, biochemical, circulatory, and pharmacological treatment of acute spinal cord injury in animals and in man.

Encephaloscopy is another area of use of the invention. It is recognized that the brain and its cavities are being successfully visualized by endephaloscopes of approximately 3 mm or more in diameter. Others are using the encephaloscope for the diagnosis and the treatment of cerebral hematoma, brain tumors and abscesses, to determine blockage of intraventricular shunts and the patency of the aqueduct of Sylvius. The encephaloscope is particularly useful in diagnosing third ventricle masses, since at the present time there are no reliable methods for determining (from clinical examination, cerebral angiography, or ventriculography) which tumor is malignant and which is benign. The needle endoscope of the invention, being three or four times smaller than the typical encephaloscope, should make encephaloscopy even safer. The microscope-telescope and electrode channel extend its other uses.

In 1964, Long et al. (Long, C. II, Brushenko, A., Pontarelli, D. A.: The fiber-optics hypodermic microscope. App. Opt. 1964, 3:1031–1032.) described a prototype hypodermic fiber-optic microscope for observing in vivo subcutaneous (fatty) tissues, muscle, and certain organs in the experimental animal and in man. Using special vital staining techniques, non-pigmented structures such as nuclei, cytoplasm and cell membranes were differentiated from each other. The investogators were able to inspect deep blood vessels and to observe the effect of disease and drugs on the exterior of these vessels. The needle endoscope will provide the same information with the additional advantage of an electrode channel for performing biopsy, stimulation and making chemical and drug studies while observing normal and diseased tissues.

The needle endoscope thus exposes the brain, spinal cord, nerve roots, peripheral nerves, muscles and other areas of the body to further safe in vivo study.

Further details of these diverse uses and of the background of the development of certain state of the art diagnostic methods of use are incorporated herein by reference to an article in Surgical Neurology, Vol. 2, No. 3, May 19, 1974, entitled "Eighteen-Gauge Microscopic-Telescopic Needle Endoscope with Electrode Channel: Potential Clinical and Research Application" by Charles P. Olinger, M.D. and R. L. Ohlhaber.

Aside from the potential medical uses, the invention is further useful in many industrial areas, such as electronics, where inspection of closed or cramped areas is required.

The invention thus provides a unique, small needle endoscope which can be used microscopically or telescopically by means of novel focusing apparatus and which provides direct visual supervision of operative treatments performed through the needle.

These and other objectives and advantages will become readily apparent from the following detailed written description and from the drawings in which:

FIG. 1 is a cross-sectional view of a needle endoscope according to the present invention;

FIG. 2 is a cross-sectional view taken along the lines 2—2 in FIG. 1;

FIG. 3 is an enlarged cross-sectional view of the forward end of the needle taken along the lines 3—3 of FIG. 1; and FIG. 4 is an enlarged end view of the forward end of the needle of FIG. 1.

Turning now to the drawings, FIG. 1 depicts a cross-sectional view of an endoscope having a scope body 10 and an elongated hollow needle 11. The scope body 10 can be of non-piece construction or of two-piece construction as shown in FIG. 1. The two-piece construction as shown in FIG. 1 includes an upper body member 12 and a lower body member 13, both of which are of substantially cylindrical outside configurations. The upper body member 12 includes a tapered portion 14 having a lower end constructed to frictionally fit over a boss 15 of the lower body member 13, the outside diameter of the boss 15 being slightly less than the inside diameter of the lower portion of the upper body member 12.

The internal surface of the upper body member 12 is threaded as at 16 to accommodate a threaded adapter member 17. In FIG. 1, adapter member 17 is particularly provided for supporting an optical objective 18 of, for example, ten power. Other adapters can be utilized for attaching the endoscope to microscopes, cameras or other recording or diagnostic instruments.

The needle 11 has a rearward or proximate end 20 which is secured to the scope body by means of a mounting member 21. The mounting member 21 is fitted to a lower portion of the lower body member 13 and may comprise luer lock means 22 for a guard needle (not shown). A forward or distal end 23 of the needle 11 extends approximately 4 inches forwardly of the scope body.

The lower scope body member 13 is provided with an internal bore 25 communicating with the proximate end 20 of the needle. Additionally, the lower scope body member 13 includes a second bore 26 in which a focus adjusting control rod 30 is disposed. Control rod 30 has a forward or lower end 31 and a rearward or upper end 32 which extends outwardly of the lower scope body member 13 and into a bore 33 within the upper scope body member 12. A spring and rod housing 35 extends upwaidly from the lower scope body 13 and is disposed over the bore 26 so as to contain the upper end 32 of the rod 30. A spring 36 is disposed between the upper end 32 of the rod and the upper end 37 of the spring and rod housing. The spring is compressed so as to urge the rod forwardly or downwardly, as shown in FIG. 1. The spring and rod housing 35 further includes a slot 38 for accommodating a lateral strut member 40 which is connected to the upper end of the rod 30.

The lower portion of the lower scope body member 13 is externally threaded as at 45 and a focus adjusting ring 46 is internally threaded and is screwed onto the threads 45 of the lower scope body member 13. The focus adjusting ring 46 includes an annular flange 47 which extends inwardly from the ring, and the lower end 31 of the control rod 30 rests on the flange 47. As the focus adjusting ring 46 is rotated about an axis through the scope body, the ring moves in a direction parallel to the axis of rotation by virtue of the threads 45 and 46. This movement of the ring causes a corresponding movement of the control rod 30 and of the strut 40 by virtue of the fact that the control rod 30 is spring biased against the flange 47 by the spring 36.

Thus as the focus adjusting ring is screwed onto the scope body, the control rod 30 is moved rearwardly or upwardly as shown in FIG. 1, carrying with it the strut 40 and compressing the spring 36. As the focus adjusting ring 46 is unscrewed from the scope body, the flange 47 moves forwardly or downwardly, as shown in FIG. 1, and the spring 36 urges the control rod 30 and strut 40 downwardly, following the flange 47. In the preferred embodiment, the control rod, the needle and the aforementioned axis of rotation of the ring are all parallel.

Turning now to FIG. 3, the hollow needle 11 is approximately 18-gauge, having an outside diameter of about 0.051 inches. The needle is formed from any appropriate material and in the preferred embodiment is a type 304 stainless steel tube, having an outside diameter of about 0.051 inches, an inside diameter of about 0.047 inches, and a wall thickness of about 0.002 inches. Disposed within the needle 11 are first tube 50 and an operative channel means comprising second tube 51 defining a channel 51a. The first tube 50 is of any suitable material such as type 304 stainless steel, and has an outside diameter of about 0.027 inches, an inside diameter of about 0.023 inches, and a wall thickness of about 0.002 inches. The second tube 51 is also made from any suitable material such as type 304 stainless steel and has an outside diameter of about 0.019 inches, an inside diameter of about 0.016 inches and a wall thickness of about 0.0015 inches. This second tube extends outwardly of the end 20 of the needle to a coupling on the scope body as will later be described.

A lens system 52 is mounted at a forward end of the tube 50 and an image transmitting bundle 53 of flexible fiber-optic rods or fibers is disposed within the tube 50.

In order to provide a very high quality resolution for viewed objects, it is desired to use the smallest flexible fiber-optic fibers available in the making of the bundle 53. Such bundles are usually produced by a drawing technique where a bundle of fibers of substantial diameters are heated and are drawn at a specific drawing pressure and rate so that the bundle is elongated and the diameter of the fibers are discussed. In this particular embodiment, each of the individual fibers of the bundle 53 is approximately 6 microns in diameter. The preferred range of individual fiber rod diameter in this bundle is approximately 4 microns to about 10 microns. Additionally, the fibers can be made from any suitable material, including glass. The bundle 53 is itself about 0.021 inches in diameter. For descriptive purposes in this application and in the claims, the term "rods" is used to define flexible optic fibers of the type referred to herein.

Further within the needle 11, and referring to FIG. 4, is disposed a plurality of illuminating transmitting fiber-optic rods or fibers 54, each having a diameter of about 0.003 inches. These rods 54 extend from a forward end 23 of the needle rearwardly and are disposed within the needle in the spaces left vacant by the tubes 50 and 51. Rods 54 exit from the needle end 20 into bore 25 and then exit from the scope body through an appropriate fitting 55. The proximate ends of the rods 54 are adapted for connection to a source of illumination (not shown) to effect the transmission and projection of cool light from the source to and beyond the distal end 23 of the needle.

The lens system 52, in a preferred embodiment, includes two lenses 60 and 61. Each of these lenses is a plano-convex lens made from any suitable material, such as glass having a glass index of 1.62. The lenses 60 and 62 are mounted within a lens mounting element or tube 62, which is press-fitted or otherwise secured, as by adhesives, to the forward end of the tube 50. The lower end of the lens mounting element is bent or rolled over as at 63 to provide a stop for the lens 61 and the lenses are further supported within the element 62 by way of adhesives, such as epoxy, or by other abutments provided within the mounting element. Also located within the lens mounting element 62 is a circular lens aperture 64 providing an opening of approximately 0.015 inches in diameter. The equivalent focal length (E.F.L.) of the lens system described is approximately 0,82 millimeters and the "F" number of the system, or the ratio of the focal length to the aperture, is approximately 2.2.

The image transmitting bundle of the fiber-optic rods is mounted within the tube 50 so that it is slidable with respect thereto. The bundle has a forward or distal end 70 operatively located with respect to the lens system 52 so that the end of the bundle 70 is positioned to pick up and transmit a composite image transmitted to the end of the bundle by the lens system.

In order that the image transmitted by the lens system may be precisely focused on the end 70 of the bundle 53, the bundle can be reciprocated, within tube 50, in opposite directions as indicated by the arrow A in FIG. 3 to compensate for objects viewed at varying distances $d$ from the end 23 of the needle 11. To this end, the image transmitting bundle 53 is approximately 6 inches long.

It extends from the position shown in FIG. 3, at the distal or forward end 23 of the needle 11, upwardly or rearwardly and outwardly of the rear end 20 of the needle within tube 50.

The image bundle extends further rearwardly through the bore 25 to a proximate end 71 within bore 33. While the fibers are individually flexible, in composition the fiber bundle is stiff enough for the reciprocation contemplated, without being so stiff as to be brittle and easily breakable. Flexibility of the bundle reduces fiber breakage due to needle bending and other stresses. The tube 50 also extends rearwardly of the end 20 of the needle but is not so long as the bundle 53, terminating at proximate end 72 near the upper portion of the lower body member 73 which fits within the scope body member 13 so as to cover the bore 25.

The upper end of the bundle 53 is connected to the strut member 40 by any suitable means so that as the strut member 40 is reciprocated, by virtue of the turning of the ring 46, the bundle 53 is also reciprocated within the tube 50 and with respect to the scope body, the needle 11, and the lens system 52, all in order to focus the instrument as will be hereinafter discussed.

The preferred embodiment has provided resolution of high contrast images of over 64 line pairs per millimeter and has resolved objects at least as small as 16 microns in size. For this resolution, the needle end 23 to object "O" distance $d$ was about one millimeter and the field diameter at the object was about 0.29 millimeters. The endoscope, by its focusing capability provides varying field of view from as small as about 0.15 millimeters. The angular field for wider field viewing at greater distanced $d$ can be as large as 41 degrees. Of course, the endoscope must be advanced toward the viewed object as the magnification increases.

In use, the preferred embodiment has a particular utility in the inspection and treatment of the nerve pathways within the spinal column. Using the following technique, radiofrequency lesions can be made in specific nerve cells or tracts in patients having intractable pain or spasticity. Particularly, a 17-gauge thin-wall lumbar puncture needle and stylet combination is introduced into the patient to provide a pathway for the needle to the spinal canal. More specifically, the puncture needle is inserted to the desired area for viewing and treatment and the stylet is removed from the puncture needle. The needle 11 of the endoscope is inserted gently through the puncture needle under direct visual control, and is introduced into the spinal canal forwardly of the puncture needle. While preparing to insert the endoscope, the operator places a finger over the hub of the puncture needle to prevent loss of cerebrospinal fluid. The areas just beyond the end 23 of the needle 11 can then be viewed visually by an observer looking through the objective 18, and the needle 11 is positioned to view the spinal cord. It will be appreciated that movement or placement of the needle is highly efficient despite anatomical variations. Insertion under visual control can avoid pial vessels.

The souruce of illumination (not shown) is activiated so that the illumination of the transmitting fibers 54 transmit light into the area. Light is reflected from the objects viewed and is transmitted to the lens system 52 toward the end 70 of the bundle 53. The image is carried from the bundle 53 to the proximate end 71 thereof and the eyepiece 18 is adjusted with respect to the scope body 10 so that it focuses on the image at end 71 of the image transmitting bundle.

The particular endoscope described above can be focused on any object such as that indicated at O in FIG. 1 which is spaced from about 0.5 millimeters to infinity from the forward end 23 of the needle 11. The space between the forward end 23 and the object O is indicated diagrammatically by $d$ in FIG. 1. Since the endoscope provides this adjustable focusing feature, the focus can be initially adjusted so as to view objects at a relatively long range from the end 23 of the needle, such as when the needle is first being inserted into the area to be inspected. Once the needle is in the precise area desired, it can be moved closer to the particular object to be viewed, such as the particular nerve cell or tract in the spinal column, and the focus can be adjusted (such as by turning the ring 46) in order to provide an in-focus view at higher magnification of the viewed object to be viewed.

A simple focus adjustment can be performed by holding ring 46 stationary and turning the scope body. If the threads 16 are properly selected (such as when the endoscope is attached to a microscope) no further adjustment of the optics rearward of end 71 of bundle 53 will be required. Once the needle end 23 is correctly positioned and the endoscope adjusted for in-focus viewing, an electrode is introduced through a coupling 80 downwardly through the channel 51a to protrude several millimeters beyond the end of the needle. Preferably, a Portnoy stainless steel electrode about 15 centimeters long and 0.305 millimeters in diameter with a teflon coating 0.127 millimeters thick (except for the forward and rearward ends) is used. The electrode can have a straight or curved tip. Once the electrode protrudes beyond the end of the needle, it is illuminated and can be visualized through the lens system 52, the bundle 53 and the objective 18. The electrode can thus be precisely placed by subsequent movement of the needle and when precisely placed, apparatus connected to the electrode can be actuated to produce radiofrequency pulses in the electrode, thereby making radiofrequency lesions in the particular nerve cells in the area of the electrode. This cuts off the pain pathway under direct visual control and supervision.

In some uses of the endoscope, some slight hemorrhaging is unavoidable. To clear the area for better viewing in these cases, a syringe can be connected to a luer lock 81, associated with the coupling 80, and warm normal saline solution can be injected through the electrode channel. Further, and to prevent fogging, the distal end of the needle can be pre-warmed by a source of dried heat or by friction with a dry surgical sponge before insertion.

The endoscope described above has a substantial number of other uses. For example, the channel 51a can be utilized for fluid sampling as by aspirating the fluid through a catheter of 30-gauge stainless steel tubing connected to syringes and inserted through channel 51a. The channel 51a can be used for injection of fluids, biopsy, action-potential studies, laser transmission, or for the introduction of medicaments. Additionally, other uses have been pointed out above.

In many of these uses, it is very important to recognize the fact that the needle 11 is of a very small diameter, which is generally acceptable for introduction into sensitive, small body areas or tissues. Despite this small diameter, the needle includes an effective means for illumination, an effective image transmitting system which can be focused to provide an in-focus image for objects which are at very greatly varying distances from the end of the needle and in addition, an operative channel which can be utilized for the treatment of internal body tissues under direct visual supervision and control. The uniqueness of the reciprocating image transmitting bundle 53 eliminates the necessity for an additional control means or channel within the needle and thereby eliminates undesired increases in the needle's diameter; the smallest diameter possible being desired as critical to useful and safe insertion of a needle-like instrument into critical, sensitive area of the body such as in various organs like the brain, the spinal cord, the eye, and the like.

These and other advantages, uses, and modifications will become readily apparent to one of ordinary skill in the art without departing from the scope of the invention and applicants intend to be bound only by the appended claims.

We claim:

1. A fiber-optic needle endoscope for viewing objects and comprising:
   a hollow elongated needle,
   an image transmitting lens system at a forward end of the needle,
   an elongated image transmitting bundle of fiber-optic rods within the needle, said bundle having a distal end near the forward end of the needle in operative disposition with respect to said lens system, and the bundle extending rearwardly from said distal end to a proximate end thereof rearwardly of the needle,
   a plurality of illumination transmitting fiber-optic rods within the needle and having distal ends at the forward end of the needle, said plurality of rods extending rearwardly and having proximate ends disposed for operative connection to a source of illumination,
   a channel means within the needle for accommodating an electrode which can be extended forwardly of the distal end of the needle and visually supervised through the image transmitting bundle, and
   means connected to the image transmitting bundle of fiber-optic rods rearwardly of the needle for reciprocating the image transmitting bundle of fiber-optic rods within the needle and with respect to the lens system in order to adjust the focus of the image transmitted to the distal end of the bundle by the lens system for a given distance between the forward end of the needle and the object to be viewed.

2. An endoscope as in claim 1 including a scope body, said needle having a rearward end attached thereto and said needle extending forwardly thereof.

3. An endoscope as in claim 2 wherein the proximate end of the image transmitting bundle of fiber-optic rods is disposed within the scope body.

4. An endoscope as in claim 3 further including optical objective means for viewing an image at the proximate end of said image transmitting bundle of fiber-optic rods, said objective means being adjustable to maintain image focus when said bundle is reciprocated.

5. An endoscope as in claim 2 wherein said means for reciprocating the image transmitting bundle of fiber-optic rods includes a control rod movably mounted in said scope body.

6. An endoscope as in claim 5 and including a strut operably connecting a rearward end of said control rod to said bundle adjacent the bundle's proximate end in order to reciprocate said bundle when said rod is moved.

7. An endoscope as in claim 6 further including a focus adjusting ring mounted on said scope body, said ring being rotatable about an axis with respect to said body and movable in a direction parallel to said needle and said axis, said ring including means for engaging a forward end of said control rod and for moving said control rod in order to move said bundle.

8. An endoscope as in claim 7 including a spring operably connected to said control rod to spring bias said control rod in a forward direction parallel to said needle, said means for engaging and moving said rod being operable to hold and to move said rod against said spring bias.

9. An endoscope as in claim 7 including a spring and rod housing means mounted within said scope body for containing said spring and a rearward end of said rod.

10. An endoscope as in claim 1 further including a first tube within said needle, said lens system mounted at a forward end of said tube at the forward end of the needle and said bundle extending through said tube from a rearward end thereof toward said lens system, said bundle being slidable within said tube.

11. An endoscope as in claim 10 wherein said channel means comprises a second hollow tube within said needle 12. An endoscope as in claim 11 wherein said illumination transmitting fiber-optic rods are disposed within said needle but outside of said first and second tubes.

13. An endoscope as in claim 12 wherein the outside diameter of the needle is approximately 0.051 inches.

14. An endoscope as in claim 12 wherein said fiber-optic rods of said image transmitting bundle each have a diameter in the approximate range of about 4 microns to about 10 microns.

15. An endoscope as in claim 12 wherein said image transmitting bundle of fiber-optic rods is approximately 0.021 inches in diameter.

16. An endoscope as in claim 12 wherein the inner diameter of said second tube is approximately 0.016 inches.

17. An endoscope as in claim 12 wherein said lens system includes at least two lenses, a lens mounting tube in which said lenses are mounted, said lens mounting tube being mounted within a forward end of said first tube, and
   aperture means mounted between said two lenses in said lens mounting tube.

18. An endoscope as in claim 17 wherein said lens aperture is approximately 0.015 inches.

19. An endoscope as in claim 18 wherein the equivalent focal length of said lens system is about 0.82 millimeters.

20. An endoscope as in claim 17 wherein the ratio of the focal length of the lens system to the aperture is approximately 2.2.

21. An endoscope as in claim 12 wherein the focus can be adjusted to provide an in-focus image of objects spaced within an approximate range of from about .5 millimeters to infinity from the forward end of the needle.

22. An endoscope as in claim 21 wherein the field of view is adjustable from about 0.15 millimeters in diameter to an angular field of about 41°.

23. An endoscope as in claim 12 wherein said illumination transmitting fiber-optic rods are each approximately .003 inches in diameter.

24. An endoscope as in claim 12 wherein said needle is approximately 4 inches long and wherein said bundle is about 6 inches long.

25. An endoscope as in claim 2 including a first tube within said needle, and extending from the forward end of said needle rearwardly and outwardly thereof, said bundle extending into and through said tube from a rearward end thereof toward said lens system and being slidable within said tube.

26. An endoscope as in claim 25 wherein said scope body includes a bore, a rearward end of said needle communicating with said bore and said first tube extending within said bore, and further including means closing an end of said bore and supporting a rearward end of said tube.

27. An endoscope as in claim 26 wherein said bundle extends outwardly of the rearward end of said tube and wherein the means for reciprocating the bundle includes means attached to that portion of the bundle extending outwardly of the tube.

28. An endoscope as in claim 2 wherein said scope body is adaptable for connection to a plurality of diagnostic instruments.

29. A fiber-optic needle endoscope for viewing objects and comprising:
a scope body,
a hollow elongated needle having an outside diameter less than about 0.051 inches and being small enough to pass through a 17-gauge thin-wall lumbar puncture needle, said elongated needle having a forward end and a rearward end attached to said scope body,
an image transmitting lens system at a forward end of the needle,
an elongated image transmitting bundle of fiber-optic rods within the needle, said bundle having a distal end operatively located near the lens system at the forward end of the needle and the bundle extending rearwardly from said distal end to a proximate end thereof rearwardly of the needle,
a plurality of illumination transmitting fiber-optic rods within the needle, and having distal ends at the forward end of the needle, said plurality of rods extending rearwardly and having proximate ends disposed for operative connection to a source of illumination,
a channel means within the needle for accommodating an electrode which can be extended forwardly of the distal end of the needle and visually supervised through the image transmitting bundle, and
means connected to the image transmitting bundle of fiber-optic rods rearwardly of the needle for reciprocating the image transmitting bundle of fiber-optic rods within the needle and with respect to the lens system in inorder to adjust the focus of the image transmitted to the distal end of the bundle by the lens system for a given distance between the forward end of the needle and the object to be viewed.

30. An endoscope as in claim 29 including a first tube within said needle and extending from a forward end of the needle outwardly of the rearward end thereof into said scope body, said bundle being disposed within said first tube and a proximate end of said bundle extending outwardly of said first tube into said scope body.

31. An endoscope as in claim 30 wherein said means to reciprocate said bundle includes a strut attached to that portion of said bundle extending outwardly of said first tube, said strut attached to means for moving said strut and said bundle.

32. An endoscope as in claim 32 wherein said means for reciprocating said bundle includes a control rod slidably mounted within said scope body, a strut connecting said rod with that portion of said bundle extending outwardly of said first tube, and a focus adjusting ring on said body for rotation about an axis, said ring moving in a direction parallel to said axis upon rotation and having a flange engaging and moving said rod in order to move said bundle in said tube when said ring is rotated with respect to said body.

33. An endoscope as in claim 32 wherein said control rod is spring biased against said flange.

34. An endoscope as in claim 30 wherein said illumination transmitting fiber-optic rods and said channel means extend rearwardly of said needle into said body and thereafter through said scope body to respective terminal ends where they are adapted respectively for connection to a source of illumination and for accommodation of treatment means.

35. A method for creating radiofrequency lesions in body tissues with a fiber-optic needle endoscope having a hollow elongated needle, an image transmitting lens system at a forward end of the needle, an elongated image transmitting bundle of fiber-optic rods within the needle, said bundle having a distal end near the forward end of the needle in operative disposition with respect to said lens system and the bundle extending rearwardly from said distal end to a proximate end thereof, a plurality of illumination transmitting fiber-optic rods within the needle and having distal ends at the forward end of the needle, said plurality of rods extending rearwardly and having proximate ends disposed for oprative connection to a source of illumination, a channel means within the needle for accommodating an electrode which can be extended forwardly of the distal end of the needle and visually supervised through the image transmitting bundle, means connected to the image transmitting bundle of fiber-optic rods rearwardly of the needle for reciprocating the image transmitting bundle of fiber-optic rods within the needle and with respect to the lens system in order to adjust the focus of the image transmitted to the distal end of the bundle by the lens system for a given distance between the forward end of the needle and the object to be viewed, and means for viewing the image at the proximate end of the bundle, said method comprising the steps of:
inserting a puncture needle and internal stylet into the body tissue,
removing the stylet,
inserting the elongated needle into the puncture needle and forwardly into the body tissue, while
viewing the image transmitted to the proximate end of the bundle, and while
adjusting the focus of the tissue object viewed by adjusting said means connected to the image transmitting bundle of fiber-optic rods and thereby reciprocating the image transmitting bundle of fiber-optic rods with respect to said elongated needle and said lens system,
inserting an electrode into said channel forwardly of the forward end of the elongated needle and placing the electrode in the body tissue in which lesions are to be created, by viewing such placement through the means for viewing the image at the proximate end of the bundle, and
generating radiofrequency impulses in said electrode to create lesions in said body tissue.

36. A method of treating body tissues with a needle endoscope having viewing means including a bundle of image transmitting fiber-optic rods operatively disposed with respect to a lens system at a forward end of the needle, and said endoscope having illumination means, the method comprising the steps of:
inserting said needle into said tissues, said needle having a forward end and a rearward end,
inserting, through said needle, an electrode into said tissues while viewing an operative end of said electrode through said needle to correctly position said electrode and forwardly of said forward end of said needle and while adjusting the focus of the endoscope to resolve viewed tissue as desired by reciprocating said bundle within said needle and with respect to said lens system in response to movement of a focus adjusting means connected in said viewing means rearwardly of the rearward end of said needle, and thereafter generating radiofrequency pulses in said electrode to create lesions in said tissue.

37. A method of treating body tissues comprising the steps of:
inserting a needle into a body near tissues to be treated, said needle having viewing means for viewing a small area of tissue microscopically under in-focus magnification and said needle being adjustable to view a larger area of tissue telescopically under lesser in-focus magnification by withdrawing said needle away from said tissue, said needle also having tissue illumination means therein and having an outside diameter of approximately 18-gauge;

focusing said viewing means to resolve the tissue viewed at a selected distance from said needle by reciprocating said viewing means with respect to said needle and in response to movement of a focus adjusting means connected to said viewing means rearwardly of a rearward end of said needle, inserting, through said needle, an electrode into said body;

viewing an operative end of said electrode through said needle and within the range of magnification provided by said viewing means;

positioning said electrode in said tissues to be treated while said electrode is under microscopic supervision, and generating radiofrequency pulses in said electrode to create lesions in said tissue.

38. A fiber-optic needle endoscope for viewing objects and comprising:
a hollow elongated needle,
an image transmitting lens system at a forward end of the needle,
an elongated image transmitting bundle of fiber-optic rods within the needle, said bundle having a distal end near the forward end of the needle in operative disposition with respect to said lens system, and the bundle extending rearwardly from said distal end to a proximate end thereof, a plurality of illumination transmitting fiber-optic rods within the needle and having distal ends at the forward end of the needle, said plurality of rods extending rearwardly and having proximate ends disposed for operative connection to a source of illumination, and means connected to the image transmitting bundle of fiber-optic rods rearwardly of the needle for reciprocating the image transmitting bundle of fiber-optic rods within the needle and with respect to the lens system in order to adjust the focus of the image transmitted to the distal end of the bundle by the lens system for a given distance between the forward end of the needle and the object to be viewed.

39. A fiber-optic needle endoscope for viewing objects and comprising:
a hollow elongated needle having a forward end and a rearward end,
an image transmitting lens system mounted at the forward end of the needle,
an elongated image transmitting bundle of fiber-optic rods within the needle, said bundle having a distal end near the forward end of the needle in operative disposition with respect to said lens system, and the bundle extending rearwardly from said distal end to
- a proximate end thereof rearwardly of said needle,
a plurality of illumination transmitting fiber-optic rods within the needle and having distal ends at the forward end of the needle, said plurality of rods extending rearwardly and having proximate ends disposed for operative connection to a source of illumination, and focus adjusting means operatively connected between the rearward end of said needle and the image transmitting bundle of fiber-optic rods rearwardly of the needle for moving the image transmitting bundle of fiber-optic rods and the combined needle, and lens system with respect to each other in order to adjust the focus of the image transmitted to the distal end of the bundle by the lens system for a given distance between the forward end of the needle and the object to be viewed.

40. An endoscope as in claim 39 wherein said elongated needle has an outside diameter of approximately 0.051 inches and further including
a channel means within the needle for accommodating an electrode which can be extended forwardly of the distal end of the needle and visually supervised through the image transmitting bundle.

* * * * *

UNITED STATES PATENT AND TRADEMARK OFFICE
CERTIFICATE OF CORRECTION

PATENT NO. : 3,941,121
DATED : March 2, 1976
INVENTOR(S) : Charles P. Olinger et al It is certified that error appears in the above-identified patent and that said Letters Patent are hereby corrected as shown below:

Column 3, line 43, insert after "surgical" the following:

--cordotomy without the problems and requirements thereof. In con- --.

Column 4, line 25, "of" should be --or--.
Column 6, line 36, "non" should be --one--.

Column 7, line 68, "discussed" should be --decreased--.
Column 8, line 28, "62" should be --61--.
Column 8, line 40, "0,82" should be --0.82--.
Column 9, line 49, "souruce" should be --source--.
Column 9, line 49, "activiated" should be --activated--.
Column 9, line 52, "to" should be --by--.

Column 13, line 59, Claim 32, "32" should be --30--.
Column 14, line 62, Claim 36, "having" should be --including--.
Column 15, line 1, Claim 36, "and" should be --end--.
Column 15, line 7, Claim 36, "in" should be --to--.

Signed and Sealed this

Eighth Day of March 1977

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,941,121
DATED : March 2, 1976
INVENTOR(S) : Charles P. Olinger et al It is certified that error appears in the above-identified patent and that said Letters Patent are hereby corrected as shown below:

Column 13, line 43, Claim 29, "inorder" should be

--order--.

Signed and Sealed this

Twenty-ninth Day of March 1977

[SEAL]

Attest:

RUTH C. MASON
*Attesting Officer*

C. MARSHALL DANN
*Commissioner of Patents and Trademarks*